Figure 7:
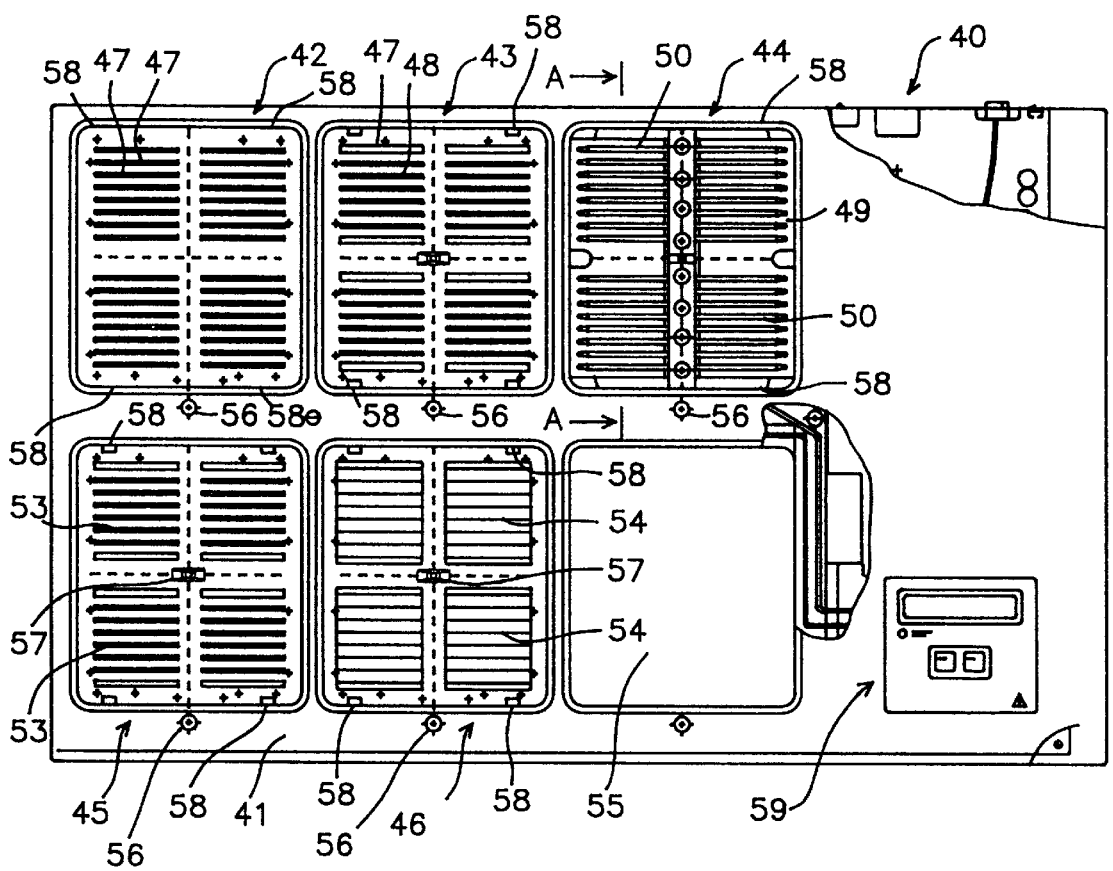

United States Patent [19]
La Motte

[11] Patent Number: 5,882,595
[45] Date of Patent: Mar. 16, 1999

[54] AUTOMATIC PROCESSING SYSTEM FOR USE IN SOLID PHASE BIOSPECIFIC BINDING AND DNA SEQUENCING TECHNIQUES

[75] Inventor: Bengt La Motte, Solna, Sweden

[73] Assignee: Pharmacia Biotech AB, Uppsala, Sweden

[21] Appl. No.: 776,019

[22] PCT Filed: Jul. 13, 1995

[86] PCT No.: PCT/SE95/00853
§ 371 Date: Jan. 17, 1997
§ 102(e) Date: Jan. 17, 1997

[87] PCT Pub. No.: WO96/02836
PCT Pub. Date: Feb. 1, 1996

[30] Foreign Application Priority Data

Jul. 18, 1994 [SE] Sweden .................................. 9402518

[51] Int. Cl.⁶ ........................ G01N 35/00; G01N 33/543; C12Q 1/68
[52] U.S. Cl. .................. 422/65; 422/63; 422/67; 422/104; 436/43; 436/46; 436/48; 436/49
[58] Field of Search .................................. 422/63, 65, 81, 422/100, 104, 67; 436/43, 46, 48, 50, 180, 49, 809, 810; 435/91.1, 91.2; 935/76, 79

[56] References Cited

U.S. PATENT DOCUMENTS

| | | | |
|---|---|---|---|
| 4,276,259 | 6/1981 | Eibl et al. ................................... | 422/71 |
| 4,738,824 | 4/1988 | Takeuchi ................................... | 422/63 |
| 4,891,321 | 1/1990 | Hubscher . | |
| 4,909,992 | 3/1990 | Bjorkman ................................ | 422/100 |
| 5,273,905 | 12/1993 | Muller et al. ........................... | 435/301 |
| 5,510,081 | 4/1996 | Edwards et al. .......................... | 422/63 |
| 5,527,673 | 6/1996 | Reinhartz et al. .......................... | 435/6 |
| 5,573,727 | 11/1996 | Keefe ....................................... | 422/63 |
| 5,624,815 | 4/1997 | Grant et al. .............................. | 435/30 |

FOREIGN PATENT DOCUMENTS

| | | |
|---|---|---|
| WO91/06659 | 5/1991 | WIPO . |
| WO92/14847 | 9/1992 | WIPO . |
| WO94/11529 | 5/1994 | WIPO . |

OTHER PUBLICATIONS

Jones et al, Bio/Technology, vol. 5, pp. 459–467 (1987).
Uber, Bio/Technology, vol. 12, pp. 80–81 (1994).

*Primary Examiner*—Long V. Le
*Attorney, Agent, or Firm*—Birch, Stewart, Kolasch & Birch, LLP

[57] ABSTRACT

A system for processing biomolecules comprising, a plurality of manifolds, each manifold having a holder portion and a number of peg members extending therefrom, a plurality of plate or strip means, each supporting a number of wells adapted to receive the manifold peg members, a processing device which comprises several processing units in the form of at least one heating plate unit adapted to receive the well plate or strip means for heating the wells thereof, at least one wash unit having a plurality of wash wells, each wash well being adapted to receive one or more manifold peg members and having at least one inlet and at least one outlet for wash liquid, and a holder device for holding a plurality of manifolds during processing in and transfer between different units of the processing device.

9 Claims, 5 Drawing Sheets

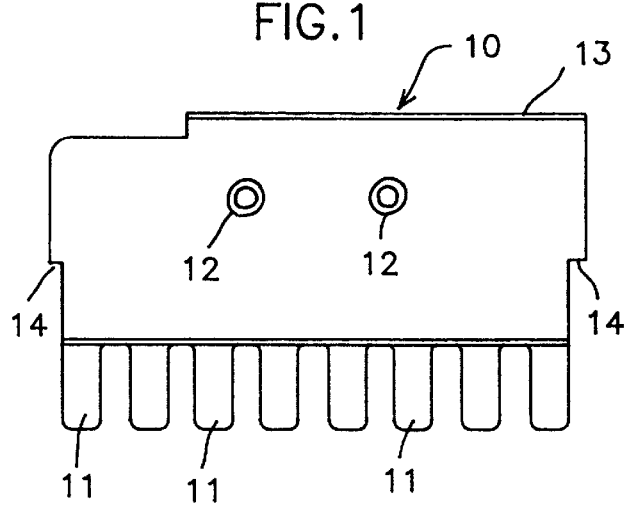
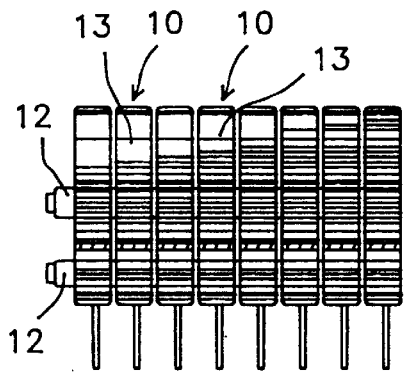
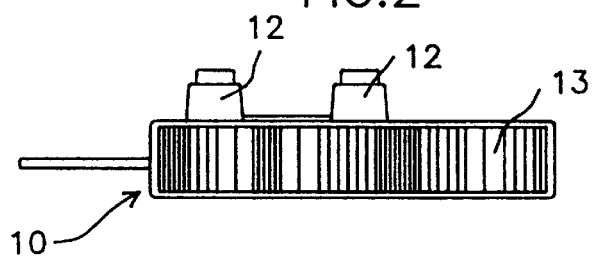
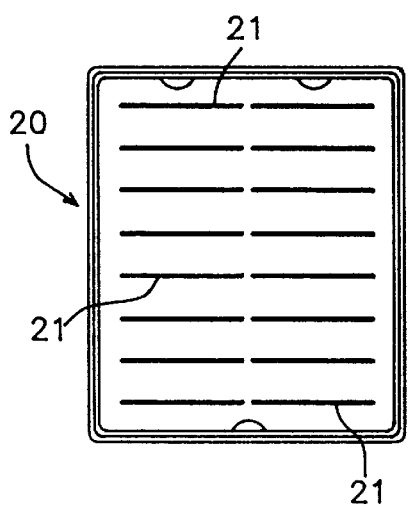
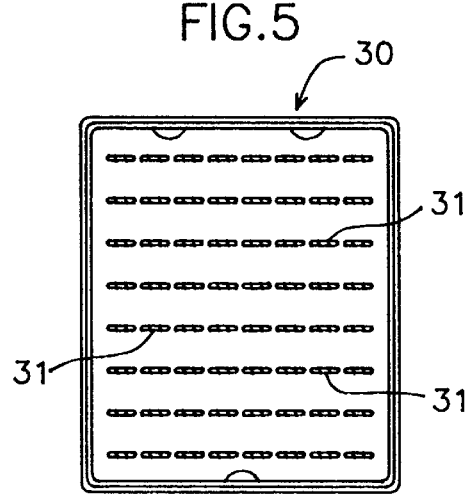
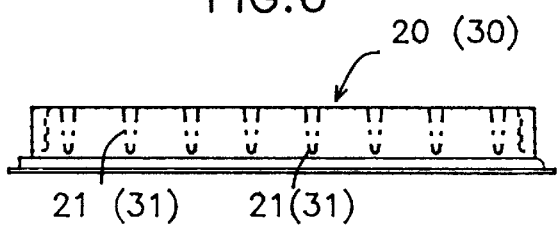

AUTOMATIC PROCESSING SYSTEM FOR USE IN SOLID PHASE BIOSPECIFIC BINDING AND DNA SEQUENCING TECHNIQUES

The present invention relates to a system for processing biomolecules, particularly in DNA sequencing.

Laboratory processes involving nucleic acid analyses are nowadays common and are often performed as a routine. Such processes include inter alia hybridization and enzymatic reactions. Often a solid phase is used for immobilization of one component of an interaction. In many cases magnetic beads have been used as the solid phase due to the simplified separation of such a solid phase. Simultaneous handling of a large number of samples has, however, still been a problem.

Our international patent application with publication number WO 94/11529 discloses a solid phase technique for nucleic acid analysis which highly facilitates the simultaneous processing of a large number of samples. This technique is based on the use of a "multi-peg" device, preferably in the form of a comb element, where each peg or tooth forms a separate solid phase member. The combs are designed to be introduced with their teeth into specially designed well plates or strips, the wells of which contain the necessary reagents.

The present invention relates to a complete processing system based on such comb and well members and comprising components specially designed for cooperation therewith, which system further facilitates the performance of nucleic acid analyses as well as other types of biomolecular interactions or analyses and makes possible the simultaneous handling and processing of a large number of samples. Such a system has the features given in the claims and is described in more detail below with regard to a non-limiting embodiment designed for nucleic acid analysis.

Figure 8:
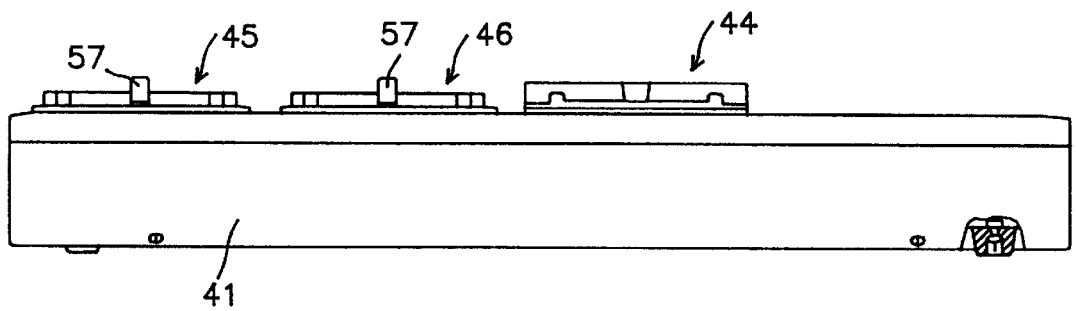
Figure 9:
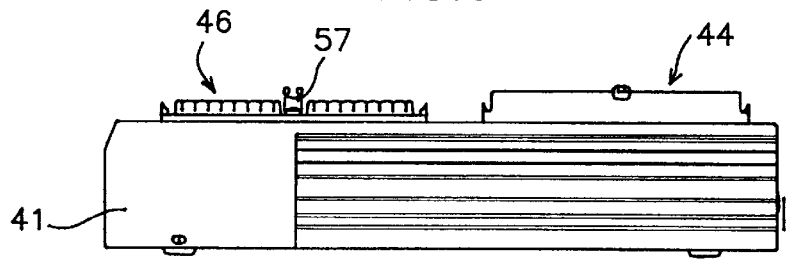
Figure 10:
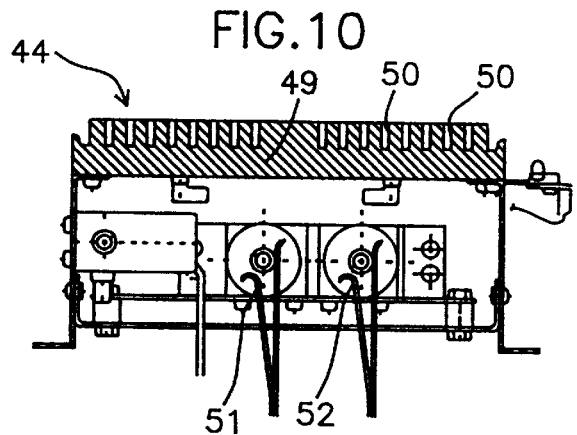
Figure 11:
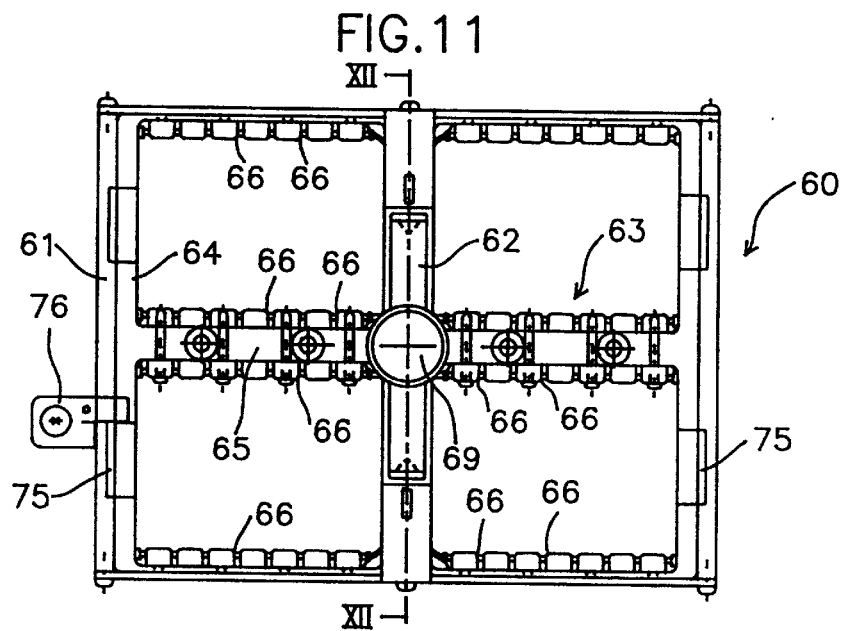
Figure 12:
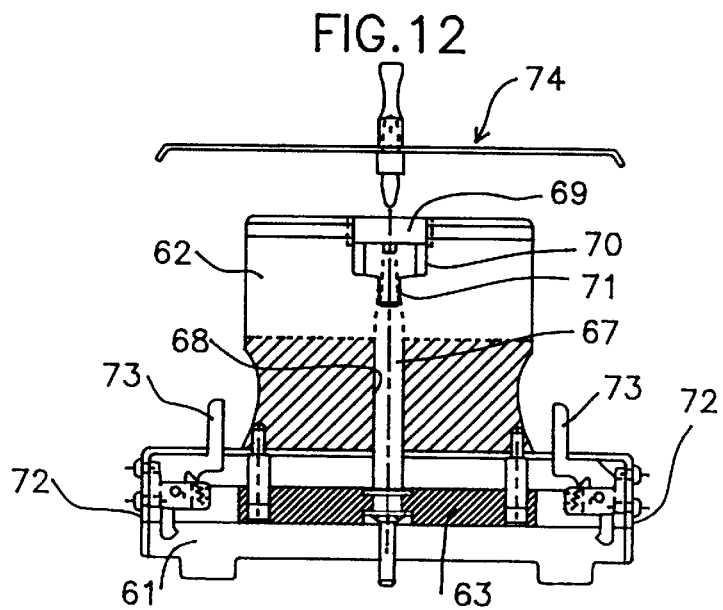
Figure 13:
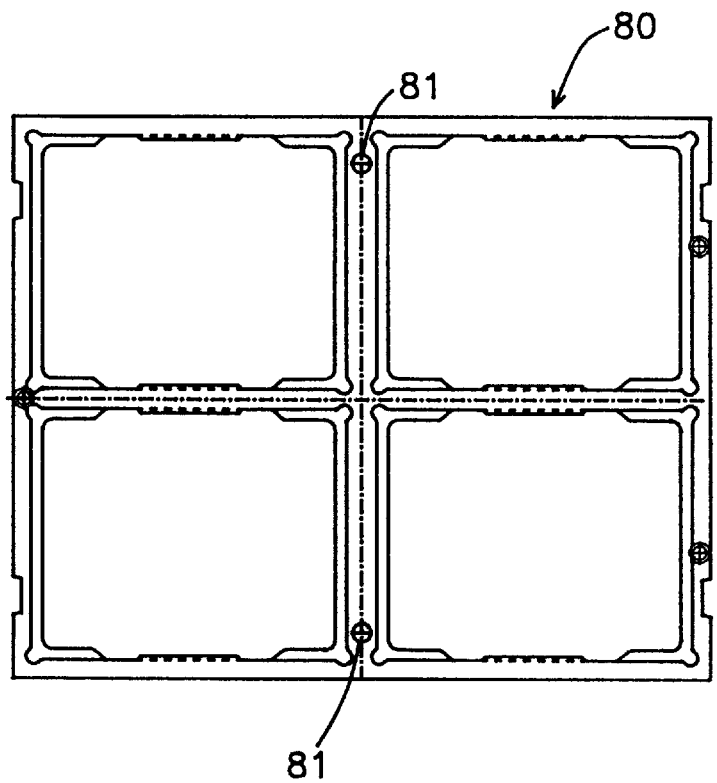
Figure 14:
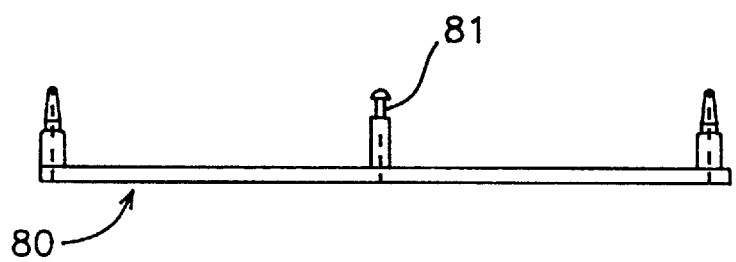
Figure 15:
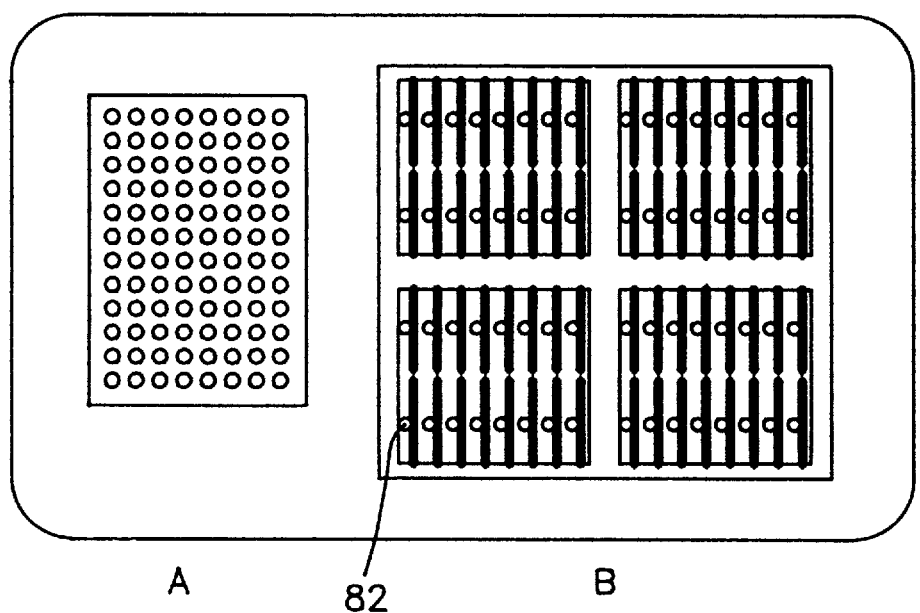

Reference is made to the accompanying drawings, wherein:

FIG. 1 is a front view of a carrier comb;
FIG. 2 is a top view of the comb in FIG. 1;
FIG. 3 is an assembly of eight combs shown in FIG. 1;
FIG. 4 is a top view of one type of well plate;
FIG. 5 is a top view of another type of well plate;
FIG. 6 is a side view of the well plates shown in FIGS. 4 and 5, respectively;
FIG. 7 is a top view, with parts broken away, of a processing unit;
FIG. 8 is a side view of the processing unit in FIG. 7;
FIG. 9 is another side view of the processing unit in FIG. 7;
FIG. 10 is a sectional view through A—A in FIG. 7;
FIG. 11 is a top view of a comb holder;
FIG. 12 is a sectional view through A—A in FIG. 11 and a lid member;
FIG. 13 is a top view of a well plate holder; and
FIG. 14 is a side view of the well plate holder in FIG. 13.
FIG. 15 is a top view of a positioning module.

The processing system shown in the figures basically comprises a carrier comb 10 (FIG. 1), two types of well plates 20 and 30 (FIGS. 4 and 5), a processing unit 40 (FIGS. 7 to 10) and a comb holder 60 (FIGS. 11 and 12). Also included in the illustrated system is a well plate holder 80 (FIGS. 13 and 14) and a positioning module (FIG. 15).

The flat comb 10 has eight teeth 11 adapted to be received in wells 21 and wells 31 of well plate 30, respectively. Comb 10 is further provided with coupling means, here in the form of two cylindrical protrusions 12 with open bottoms and a tip with reduced diameter which will fit into the open bottom of an aligned comb 10. Thereby several combs may be snapped together as illustrated in FIG. 3, which shows an assembly of eight combs 10. A top flange 13 is provided on comb 10 for labelling purposes, such as by optically readable bar codes. Each side edge of the comb 10 has a step portion 14 to permit the comb to be held in comb holder 60 as will be described below.

Well plate 20 has, in the illustrated case, eight rows of wells 21, each row of which has two wells. Each well 21, which may be dimensioned to hold, e.g., a liquid volume of about 100 μl, is designed to receive four comb teeth 11 and is therefore hereinafter sometimes referred to as "four teeth well". Similarly, well plate 30 has eigth well rows, each row having eight wells 31 designed to receive a single well comb tooth 11, and well type 31 is therefore hereinafter sometimes referred to as "one tooth well". Each well 31 may, e.g., be dimensioned to hold a liquid volume of about 20 μl.

The integral processing unit shown in FIGS. 7 to 9 comprises a chassis 41 in which, in the illustrated, five processing modules or "stations" are mounted, viz. a "capture" station 42, a "denaturation" station 43, a "wash" station 44, an "annealing" station 45, and a "sequencing reaction" station 46.

The capture station 42 is a plate for thermal control, i.e. heating or cooling, with four groups of eight vertical heating or cooling flanges 47. Each heating flange 47 has a central recess for receiving one row of wells 21 of a well plate 20, such that four well plates may be placed on the heating plate simultaneously with the wells 21 in thermal contact with the heating flanges.

The denaturation station 43 has a similar structure to the capture station 42 and also comprises a plate with four sets of eight flanges 48 for receiving a respective well plate 21. The denaturation station 43 may or may not be heatable.

Wash station 44 comprises, as is best shown in FIG. 10, a plate 49 with four groups of eight elongated recesses 50. Each recess 50 is adapted to receive the eight teeth 11 of a comb 10. Means are further provided for pumping wash liquid separately through each recess, e.g., from a central inlet to outlets at the ends of each recess, in the illustrated case two pumps 51, 52 for inlet and outlet, respectively. The illustrated wash station 44 may thus process 32 combs 10 simultaneously.

Annealing station 45 has a similar structure to the denaturation station 43 and comprises a plate with four sets of eight flanges 53, each set adapted to receive a well plate 21. In the same way as for the capture station 42, means are provided for controlled heating and cooling of flanges 53.

The sequencing reaction station 46, finally, is also a heating plate with four sets of eight recesses 54. Each recess 54 is designed to receive one row of well plates 31. The illustrated design of heating plate, with recesses 54 provided in a solid plate rather than in heating flanges as in stations 42, 43 and 45 described above, may be used in this station since no rapid temperature changes are required here, as will be described below.

Reference numeral 55 indicates a free "set aside" area.

Reference numerals 56 at stations 42–46 indicate light signal means, the function of which will be described below.

Processing stations 43, 45 and 46 all have a central lock member 57 for cooperation with the comb holder 60 as will be described below. Further, all the processing stations 42–46 have four protrusions 58 for aligning the comb holder 60 therewith, as will also be described below.

The processing unit 40 is adapted to be connected to a computer for the control of the different processing stations, such as heating and wash liquid flow, and operation of the unit is performed via a small key pad and display 59.

Comb holder 60 shown in FIGS. 11 and 12 is designed for the transfer of combs 10 between the different processing stations. Holder 60 comprises a horizontal frame 61 attached to a handle 62. A comb rack 63 is mounted inside frame 61 to be vertically movable in relation to the frame. Comb rack 63 is here formed by a rectangular frame 64 with a central cross bar 65 normal to handle 62. Recesses 66 in the cross bar 65 and the opposite frame parts are designed to receive and hold combs 10 via the stepped vertical side edges 14 thereof (FIG. 1). Four comb holding sections, each with eight opposed recesses 66, are defined by the cross bar 65 and the handle 62, each section thus being capable of holding eight combs.

Comb rack 63 is supported by a vertical bar 67 extending through a bore 68 in handle 62. The upper end of bar 67 is in turn rotatably connected to a knob member 69 received in a recess 70 in the handle. A vertical plate-like extension 71 of the knob member 69, when aligned with the recess, fits into the upper part of bore 68 and may be received therein, as is shown in FIG. 12, the comb rack 63 thereby being held a first, lowered position. In this position, the teeth 11 of each supported comb 10 are inserted into a corresponding well 21 or 31 of a well plate 20 or 30, respectively, placed on any one of the processing stations when the comb holder 61 is properly placed on that station. By lifting knob member 69, and thereby comb rack 63, and then turning the knob to place the extension 71 out of alignment with its recess, the comb rack will be held in a second, raised position.

The comb holder 60 is further provided with two opposed spring-biased hook means 72, each having an operation lever 73, for cooperation with pin members 81 on the well plate holder 80, as will be described below.

An exemplary use of the above described processing system for DNA sequencing of PCR amplified DNA fragments to be sequenced will now be described.

Four well plates 20 with PCR amplified biotinylated DNA fragments to be sequenced, one strand of which is biotinylated, are supported by the well plate holder 80. Each well 21 may contain a different DNA fragment.

Comb holder 60 is loaded with combs 10, to the teeth 11 of which streptavidin has been immobilized, the comb rack 63 being held in the raised position. The comb tops may be covered by two lids 74 (FIG. 12) placed over the combs on either side of the handle 62. The comb holder 60 is then placed correctly on the well plate holder 80 so that the hook means 72 engage with the pin members 81, and the whole assembly is then moved to capture station 42 of the processing unit. The combs 10 have previously been provided with bar codes, and these are now read into the system computer to relate each comb to the amplification product from a particular sample. The indicator light 56 flashes to indicate that this station is to be used, and the display 59 may, e.g., indicate "Go to position one".

Next, the comb holder 60 is aligned with the capture station 42 and placed thereon so that the protrusions 58 fit into recesses 75 in the holder frame 61. The well rows of the well plates 20 will be received in the recesses of the heating flanges 47. The comb rack 63 is then lowered to enable the comb teeth 11 of each comb 10 to be introduced into the corresponding wells 21. When the comb rack is in the lowered position, an activator member 76 supported by the comb rack contacts the chassis 41 to effect a switch function starting the capture process. To this end, activator member 76 may, for instance, contain a magnet which activates an aligned Hall element mounted in the chassis. The capture process, in which biotinylated DNA fragments are bound to the streptavidin coated comb teeth, may, for example, advantageously consist of two heating cycles 20°–80° C. completed during 30 minutes. Such cycled heating will enhance the capture process. During the capture process, the light indicator 56 emits a steady light and the display may show the station number and remaining process time. When the predetermined process time has passed, which may be indicated by a discrete sound signal, the capture function will stop. Simultaneously, the light signal stops. Instead the light signal indicator 56 at the denaturation station 43 will start to flash and and the display may, e.g., show "Go to position 2".

The comb holder 60 is then released from the well plate holder 80 by raising the comb rack 63 to the upper position and pressing the levers 73 of hook means 72 towards each other to disengage them from the pin members 81, whereupon the comb holder is moved to the denaturation station 43.

Well plates 20, which have the necessary denaturation agent in the wells 21 thereof for release of the non-biotinylated DNA-strand from the DNA fragments just captured on the comb teeth, have previously been placed on the denaturation station 43 with the well rows received in the respective heating flange recesses. Preferably, the well plates have been prepared in advance with predispensed anhydrated reagents, e.g. glassified, so that only water need to be added before use.

The comb holder 60 is then aligned with and placed on the denaturation station 43, and the comb rack is lowered to insert the comb teeth 11 into the respective wells 21. The lower end of the bar 67 will then engage with the lock member 57 to prevent removal of the comb holder 60 if the comb rack has not been raised to its upper position where the comb teeth are above the wells.

As before, the light indicator 56 will have a steady light during the process, which may last for, e.g., 5 min. When this time has passed, the light will go out, a sound signal buzz, and the display may show, e.g., "Go to position 3".

In the same was as described above, the comb holder 60 is then moved to the wash station, where the comb teeth are washed for, e.g., 3 min.

Comb holder 60 is then transferred to the annealing station 45 where well plates 20 with sequencing primer solutions in the wells 21 have been placed on the heating flanges 53. Preferably, the wells 21 have been predispensed with anhydrated primer mixes so that only water is added before use. Annealing of primers to the single stranded DNA fragments immobilized on the comb teeth may, for example, be performed by heating at 60° C. for 10 min and then controlled cooling for 10 min to room temperature.

The comb holder 60 is finally moved to the sequencing reaction station 46, where well plates 30 with "one tooth wells" have been placed on the heating plate with the wells 31 received in the recesses 54. The wells 31 contain the necessary sequencing mixes, preferably predispensed in anhydrated form to only require the addition of water at the time of use.

When the sequencing reactions are completed, the combs 11 are brought to an automated sequencer, e.g., an A.L.F.™ DNA Sequencer (Pharmacia Biotech AB, Uppsala, Sweden) where the primer extension products on the comb teeth are released into the sample wells of the sequencer.

As a further embodiment, a positioning module, A in FIG. 15, can be included in the system for processing biomolecules according to the invention. The positioning module, A, is situated before the processing modules or "stations" shown in FIG. 7 and described above. In FIG. 15 one such "station" is indicated with B. The positioning module consists of a metal plate with holes designed for receiving the wells of a micro-titre plate. The size of the metal plate is that of standard micro-titre format, both concerning the number of wells as well as the distance between the wells. In the bottom of each hole there is a light-emitting diode. When a micro-titre plate has been placed on the positioning module it is possible to see through the bottom of each well if the light-emitting diode is switched on. This principle is used to show from which well the sample shall be brought. The processing module or "station", B, shown in FIG. 15 comprises four well plates of the type shown in FIG. 4. Each well plate has 2×8 wells 21 and at the side of each well there is a light-emitting diode 82.

When the positioning module is used a micro-titre plate containing samples of e.g. PCR amplified DNA fragments is placed on the positioning module A. Four empty well plates are placed on the processing module B. The computer programme controlling the positioning is activated and some of the light-emitting diodes are swithed on. By means of the light-emitting diodes on the positioning module and on the processing module respectively, and the displayed-information text on the display panel, information is obtained from which position on the positioning module to which position of the processing module the sample shall be moved. A common operation is to move samples from one horizontal row in the micro-titre plate to a horizontal row in the well plate by means of a 8-canal pipette.

As is readily seen from the above, the described processing system prevents mix-up of samples, prevents contamination between samples and is easy to operate.

The invention is, of course, not restricted to the embodiments specifically described above and shown in the drawings, but many changes and modifications may be made without departing from the inventive concept as defined in the following claims.

I claim:

1. A system for processing biomolecules, comprising:

a plurality of manifolds (10), each manifold having a holder portion and a number of peg members (11) extending therefrom, a plurality of plate or strip means (20, 30), each supporting a number of wells (21, 31) adapted to receive the manifold peg members (11), a processing device (40) which comprises a plurality of processing modules (42–46) in the form of
   (i) at least one module for thermal control (42) adapted to receive the well plate or strip means (20, 30) for heating or cooling the wells (21, 31) thereof,
   (ii) at least one wash module (44) having a plurality of wash wells (50), each wash well (50) being adapted to receive one or more manifold peg members (11) and having at least one inlet and at least one outlet for wash liquid, and a holder device (60) for holding a plurality of manifolds (10) during processing in and transfer between different modules of the processing device (40), and computer means for controlling the function of the processing device (40), and indicator means (56) controlled by said computer means to indicate when and on which processing module (42–46) each processing step in a sequence of processing steps is to be performed.

2. The system according to claim 1, characterized in that said manifolds are comb elements (10) with teeth (11).

3. The system according to claim 1 or 2, characterized in that the holder device (60), when placed on a processing module (42–46), is arranged to hold the manifolds (10) in two alternative vertical positions above a well plate or strip (20, 30) received on the module, a lower position in which the manifold peg members (11) are inserted into the wells (21, 31), and an upper position in which the peg members (11) are above the wells (21, 31).

4. The system according to claim 1, characterized in that the holder device (60) comprises activator means (74) which, when the holder device (60) is placed on a processing module (42–46) and the manifolds (10) are brought to the lower position, activate start of the process at the processing module (42–46).

5. The system according to claim 1, characterized in that each manifold (10) or group of manifolds are labelled by optically readable labels for identification of different manifolds (10).

6. The system according to claim 1, characterized in that the system is adapted for sequencing of nucleic acid fragments and comprises:

a first, heatable plate module (42) for performing capture of nucleic acid fragments on manifold peg members (11), a second plate module (42), which optionally may be heated, for performing denaturation of captured double stranded nucleic acid fragments into immobilized single stranded nucleic acid fragments, a wash module (44) for washing manifold peg members (11) which have been subjected to the denaturation step, a third, heatable plate module (45) for performing annealing of sequencing primers to single stranded nucleic acid fragments immobilized to manifold peg members (11), and a fourth, heatable plate module (46) for performing sequencing reactions on the primer annealed nucleic acid fragments immobilized to manifold peg members (11).

7. The system according to claim 1, characterized in that the system comprises well plates or strips (20, 30) where the wells (21, 31) contain predispensed reagents in anhydrated form.

8. The system according to claim 1, characterized in that the manifolds (10) are provided with coupling means (12) for enabling coupling of two or more manifolds (10) to form an assembly thereof.

9. The system according to claim 5, wherein the optically readable labels are bar codes.

* * * * *